United States Patent
Stemmer (10) Patent No.: US 9,841,476 B2
(45) Date of Patent: Dec. 12, 2017

(54) METHOD AND APPARATUS FOR MAGNETIC RESONANCE IMAGING

(71) Applicant: Siemens Aktiengesellschaft, Munich (DE)

(72) Inventor: Alto Stemmer, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 15/074,250

(22) Filed: Mar. 18, 2016

(65) Prior Publication Data
US 2016/0274202 A1 Sep. 22, 2016

(30) Foreign Application Priority Data

Mar. 19, 2015 (DE) .......................... 10 2015 204 953

(51) Int. Cl.
*G01R 33/3875* (2006.01)
*A61B 5/055* (2006.01)
(Continued)

(52) U.S. Cl.
CPC .......... *G01R 33/3875* (2013.01); *A61B 5/055* (2013.01); *G01R 33/56563* (2013.01); *G01R 33/243* (2013.01); *G01R 33/543* (2013.01)

(58) Field of Classification Search
CPC ................ G01R 33/243; G01R 33/543; G01R 33/3875; G01R 33/56563; A61B 5/055
See application file for complete search history.

(56) References Cited

U.S. PATENT DOCUMENTS

| 7,315,168 B2* | 1/2008 | Rapoport | G01R 33/3875 324/320 |
| 7,554,327 B2* | 6/2009 | Dewdney | G01R 33/3875 324/319 |

(Continued)

FOREIGN PATENT DOCUMENTS

EP 1 845 387 A2 10/2007

OTHER PUBLICATIONS

Sengupta, et al: "Dynamic B0 shimming at 7 tesla",: MORM, vol. 29, pp. 483-496, (2011).

(Continued)

*Primary Examiner* — Dixomara Vargas
(74) *Attorney, Agent, or Firm* — Schiff Hardin LLP (57) ABSTRACT

To enable improved adjustment of at least one shim channel for magnetic resonance imaging of an examination region of an examination object by operation of a magnetic resonance apparatus that has a shim arrangement with a first shim channel volume having at least one first shim channel and a second shim channel volume having at least one second shim channel, the examination region is divided into multiple of sections, multiple first shim parameter sets are determined for the at least one first shim channel, with one first shim parameter set among the multiple first shim parameter sets being ascertained for each of the multiple sections, a second shim parameter set is ascertained for the at least one second shim channel, taking into account the ascertained multiple first shim parameter sets, and magnetic resonance image data of the examination region are acquired, but before this acquisition, the at least one second shim channel is adjusted using the second shim parameter set and the at least one first shim channel is adjusted for acquiring the magnetic resonance image data from a specific (Continued)

section of the multiple sections using a first shim parameter set ascertained for that specific section.

13 Claims, 4 Drawing Sheets (51) Int. Cl.
    *G01R 33/565* (2006.01)
    *G01R 33/24* (2006.01)
    *G01R 33/54* (2006.01)

(56) References Cited

U.S. PATENT DOCUMENTS

| | | | | |
|---|---|---|---|---|
| 7,592,812 B2 * | 9/2009 | Ikedo | ............... | G01R 33/3875 324/319 |
| 7,907,767 B2 * | 3/2011 | Bekku | ............... | G01R 33/3875 382/131 |
| 8,362,771 B2 * | 1/2013 | Dornhaus | ............ | G01R 33/243 324/309 |
| 8,362,778 B2 * | 1/2013 | Slade | ............... | G01R 33/3873 324/318 |
| 8,519,712 B2 * | 8/2013 | Chen | ................ | G01R 33/3875 324/318 |
| 9,075,120 B2 * | 7/2015 | Shinagawa | ........ | G01R 33/3815 |
| 9,377,517 B2 * | 6/2016 | Witschey | ........... | G01R 33/3875 |
| 9,606,205 B1 * | 3/2017 | Ito | ..................... | G01R 33/4838 |
| 2003/0144589 A1 | 7/2003 | Roell | | |
| 2005/0264286 A1 | 12/2005 | Harder | | |
| 2008/0088307 A1 | 4/2008 | Dewdney et al. | | |
| 2009/0232410 A1 | 9/2009 | Dahnke et al. | | |
| 2012/0098541 A1 | 4/2012 | Konijn et al. | | |
| 2012/0235681 A1 | 9/2012 | Stemmer | | |

OTHER PUBLICATIONS

Blamire et al: "Dynamic Shim Updating: A new approach towards optimized whole brain shimming", MRM, vol. 36, pp. 159-165, (1996).

Morell et al.: "Dynamic Shimming for Multi-Slice Magnetic Resonance Imaging", MRM, vol. 38, pp. 477-483, (1997).

de Graaf et al,: "Dynamic Shim Updating (DSU) for Multislice Signal Acquisition", Magnetic Resonance in Medicine, vol. 49, No. 3, pp. 409-416 (2003).

* cited by examiner

METHOD AND APPARATUS FOR MAGNETIC RESONANCE IMAGING

BACKGROUND OF THE INVENTION

Field of the Invention

The invention concerns a method for magnetic resonance imaging, a magnetic resonance apparatus and a non-transitory, computer-readable data storage medium for implementing such a method.

Description of the Prior Art

In a magnetic resonance apparatus, also called a magnetic resonance tomography system, the body of an examination person, in particular a patient, to be examined is situated in a scanner of the apparatus that has a basic field magnet that exposes the patient to a relatively high basic magnetic field, for example of 1.5 or 3 or 7 tesla. In addition, gradient pulses are activated by a gradient coil arrangement. Radio-frequency pulses, for example excitation pulses, are then emitted by a radio-frequency antenna unit by suitable antenna devices, and this leads to the nuclear spins of specific atoms, excited in a resonant manner by these radio-frequency pulses, being tilted by a defined flip angle with respect to the magnetic field lines of the basic magnetic field. When the nuclear spins relax, radio-frequency signals, known as magnetic resonance signals, are radiated, which are received by suitable radio-frequency antennae and then processed further. Finally, the desired image data can be reconstructed from the raw data acquired in this way.

For a specific scan a specific magnetic resonance sequence, also called a pulse sequence, should be emitted that is a sequence of radio-frequency pulses, for example excitation pulses and refocusing pulses, and appropriate gradient pulses that are emitted in a coordinated manner in gradient axes in respective directions. At a time appropriate therewith, readout windows are set, which specify the periods in which the induced magnetic resonance signals are detected.

The homogeneity of the basic magnetic field in an examination volume is very important in magnetic resonance imaging by operation of the magnetic resonance scanner. Even small deviations in the homogeneity can lead to large deviations in the frequency distribution of the nuclear spins, so poor quality magnetic resonance image data are recorded. For example, magnetic resonance recording methods, such as echo planar imaging or spiral imaging, place high demands on the homogeneity of the basic magnetic field.

The examination object to be recorded itself constitutes a source of inhomogeneity. If, for example, a person to be examined is introduced into the magnetic resonance scanner, the material of the body interferes with the homogeneity of the basic magnetic field.

To counter this problem it is known to use an adjustable shim arrangement. With this shim arrangement, a shim process, known as "in vivo shimming", can be carried out individually for different examination objects. In this shim process, first a local B0 field in the examination region is conventionally scanned, and a B0 field map, also called B0 map, is created. Constant shim currents (DC offset currents), which flow through gradient coils of the magnetic resonance scanner, are ascertained using the B0 field map. Furthermore, using the B0 field map, currents can be calculated for specific shim channels of a higher order, which can compensate the local field distortions. After adjustment of these currents a resonance frequency is usually ascertained in a frequency adjustment for desired spectral components of an examined tissue, in particular of protons bound to water. The DC offset shim currents and/or the currents for the shim channels of a higher order and/or the resonance frequency can then form a shim parameter set which is used for acquiring magnetic resonance image data.

It is known that compensation of local field distortions functions all the more completely the smaller a volume is in which the basic magnetic field is to be homogenized. It therefore make sense to ascertain various shim parameter sets for multiple sections of the examination region separately and to adjust the shim arrangement differently using the various shim parameter sets for acquiring magnetic resonance image data from the multiple sections. Rapid switching-over of the shim currents and resonance frequency during a runtime of the magnetic resonance sequence for acquiring the magnetic resonance image data on a sequence-dependent timescale of a few milliseconds to a few seconds may be necessary. For this reason, this type of shim process is also conventionally called dynamic shimming.

Dynamic shimming is described, for example, in Blamire et al., "Dynamic Shim Updating: A New Approach Towards Optimized Whole Brain Shimming", 1996, MRM, 36, 159-165 and in the document Morrell et al., "Dynamic shimming for Multi-Slice Magnetic Resonance Imaging", 1997, MRM, 38, 477-483.

The accuracy with which local inhomogeneities of the basic magnetic field are compensated depends on the number and order of existing and usable shim channels. In modern MR systems, linear shim terms are usually generated, for example in the three directions, by DC offset shim currents of the three gradient coils. Due to the linear field characteristic in the gradient directions, the gradient coils filled with the static shim currents can then be called shim channels of the first order. Furthermore, magnetic resonance devices can have dedicated shim coils. These dedicated shim coils can then form shim channels of a higher order, for example of the second order. Shim channels of this kind are often constructed such that the compensation fields which they generate can be described by spherical harmonics. These shim channels can therefore generate compensation fields of a higher order. For example, typical shim channels of the second order have five shim coils.

The gradient coils and associated gradient amplifiers are typically designed such that the gradient fields can be varied on a timescale of a few microseconds, such as roughly ten microseconds. This is usually sufficient for dynamic shimming. By contrast, the field of shim channels of a higher order is typically adjusted only after a settle time on the order of a second. This is frequently not enough for dynamic shimming. The cause of this can be due to hardware design because faster adjustment of these shim channels demands more powerful amplifiers and/or possibly conductors having low resistance. This can increase the cost of the magnetic resonance apparatus. The space that is available to the shim coils of the shim channels of a higher order may also be limited.

For these reasons, it is often the case that only the shim channels of the first order, namely conventionally the gradient coils, and/or an RF center frequency resulting from a frequency adjustment, are dynamically switched in a dynamic shim process. Therefore, typically only the currents in the shim channels of the first order vary during the runtime of the magnetic resonance sequence. In the shim channels of a higher order a current is conventionally adjusted once before the scan. This current should then be kept constant across the scan. The constant DC offset shim current can correspond to a device-specific tune-up value or be ascertained in a specific adjustment carried out in advance for the examination object.

SUMMARY OF THE INVENTION

An object of the invention is to enable an improved adjustment of at least one shim channel for magnetic resonance imaging.

The inventive method for magnetic resonance imaging in an examination region of an examination object by operation of a magnetic resonance scanner that has a shim arrangement having a first shim channel volume having at least one first shim channel and a second shim channel volume having at least one second shim channel, includes the following steps.

The examination region is divided into multiple sections.

Multiple first shim parameter sets are ascertained for the at least one first shim channel, with one first shim parameter set, among the multiple first shim parameter sets, being ascertained for each of the multiple sections.

A second shim parameter set is ascertained for the at least one second shim channel by taking into account the multiple first ascertained shim parameter sets.

Magnetic resonance image data are acquired from the examination region of the examination object, wherein, before acquiring the magnetic resonance image data, the at least one second shim channel is adjusted using the second shim parameter set and the at least one first shim channel is adjusted for acquiring the magnetic resonance image data from a specific section of multiple sections using the first shim parameter set ascertained for that specific section.

The examination region, also called field of view (FOV), is a volume that is mapped in the recorded magnetic resonance image data. The examination region is typically defined by a user, for example on a topogram (localizes). Of course the examination region can alternatively or additionally be defined automatically, on the basis of a chosen protocol. The multiple sections of the examination region in combination produce the entire examination region. The examination object can be a patient, training person, an animal or a phantom. The acquired magnetic resonance image data are supplied, i.e. displayed, for a user on a display monitor and/or stored in a database.

According to the invention, the examination region has multiple sections, namely at least one first section and one second section. The examination region can of course have further sections in addition to the first and second sections. A single excitation slice of the magnetic resonance sequence can be a section of the examination region. The number of sections of the examination region thus can be equal to the number of slices of the examination region. Of course larger sections of the examination region having, for example, a number of slices, or smaller sections, are also conceivable. The magnetic resonance image data are acquired separately for the respective sections of the multiple sections of the examination region. The present invention is relevant in particular for those sequence techniques in which time intervals in which magnetic resonance image data are acquired from the first section alternate with those time intervals from which magnetic resonance image data are acquired from the second section on a timescale that is small compared to an adjustment time of the at least one second shim channel.

The first shim channel volume can encompass one first shim channel or a number of first shim channels. A first shim channel of the first shim channel volume is formed by a gradient coil of the magnetic resonance device. It is also conceivable for a first shim channel of the first shim channel volume to be formed by a dedicated shim coil of the shim arrangement. The at least one first shim channel can generate shim fields of the first order, in particular linear shim fields. Theoretically, it is also conceivable for a first shim channel of the first shim channel volume to generate shim fields of a higher order, for example of the second order.

As already described, during acquisition of the magnetic resonance scan data the at least one first shim channel can be supplied with different shim currents. The shim currents in the at least one first shim channel thus can be switched-over for acquisition of magnetic resonance scan data from different sections of the examination region. Therefore, different first shim parameters sets of the multiple first shim parameter sets can be used to acquire the magnetic resonance image data from a first section and a second section of the examination region. For example, the at least one first shim channel can be supplied with different shim currents for acquisition of magnetic resonance image data from different slices of the examination region. In this way a field contribution can be varied for a homogenization of the basic magnetic field due to the shim currents flowing through the at least one first shim channel during acquisition of the magnetic resonance scan data. The at least one first shim channel is therefore designed for dynamic shimming.

The second shim channel volume can be one second shim channel or multiple second shim channels. A second shim channel of this kind of the second shim channel volume is formed in particular by a dedicated shim coil. The at least one second shim channel can generate shim fields of a second or higher order. Theoretically, it is also conceivable for a second shim channel of the second shim channel volume to generate shim fields of the first order.

As already described, during acquisition of the magnetic resonance scan data the at least one second shim channel is always supplied with the same shim currents. The at least one second shim channel thus can be filled with the same shim currents for acquisition of magnetic resonance image data from different sections of the examination region. In this way, a field contribution can remain constant for a homogenization of the basic magnetic field due to the shim currents flowing through the at least one second shim channel during acquisition of the magnetic resonance image data. The at least one second shim channel thus is not designed for dynamic shimming.

A shim parameter set can represent adjustments for controlling the shim arrangement of the magnetic resonance scanner, in particular at least one specific shim channel of the shim arrangement. For example, a shim parameter set can define a current in the at least one shim channel. During recording of the magnetic resonance image data, a shim control amplifier can then load the at least one shim channel with the current defined by the shim parameter set. Furthermore, a shim parameter set can designate an appropriate value for the center frequency and/or resonance frequency. In this way a separate frequency adjustment, for example, can be omitted.

The multiple first shim parameter sets for the at least one first shim channel can be ascertained, for example, using a first B0 field map, as described above. According to the inventive approach, the multiple first shim parameter sets are then incorporated in the ascertaining of the second shim parameter set for the at least one second shim channel. The multiple first shim parameter sets thus can constitute input parameters for an algorithm that is used to ascertain the second shim parameter set.

The multiple first shim parameter sets are designed differently from each other. They have, for example, different current values for the at least one shim channel. The multiple first shim parameter sets therefore include a first section shim parameter set and a second section shim parameter set. The at least one first shim channel is therefore advantageously adjusted using the multiple first shim parameter sets such that, for acquiring magnetic resonance image data from a first section of the multiple sections, the at least one first shim channel is adjusted using the first section shim parameter set and, for acquiring magnetic resonance image data from a second section of the multiple sections, the at least one first shim channel is adjusted using the second section shim parameter set. A first shim parameter set of the multiple first shim parameter sets is ascertained for each section of the multiple sections.

By contrast, a single second shim parameter set is ascertained for the at least one second shim channel for acquiring the magnetic resonance image data. Using this single second shim parameter set the at least one second shim channel can then be adjusted throughout acquisition of the magnetic resonance image data from the plurality of sections of the examination region, in particular from the first section and the second section. In specific applications it is also conceivable for the at least one second shim channel to be supplied with different shim currents during acquisition of the magnetic resonance image data. This can mean that multiple second shim parameter sets are ascertained for the at least one second shim channel, such as by taking into account the multiple first shim parameter sets.

The inventive approach has the advantage that consideration of the multiple first shim parameter sets when ascertaining the second shim parameter set can lead to a particularly advantageous second shim parameter set. The second shim parameter set thus can have optimum shim currents for the at least one second shim channel. The at least one second shim channel cannot be switched fast enough, in particular for dynamic shimming. Using the inventive method, inhomogeneities in the basic magnetic field can be significantly reduced, and optimally compensated, by a total compensation field embodying a dynamically switched compensation field of the at least one fast-switchable first shim channel, and a constant compensation field of the at least one second shim channel of a higher order. In this context a scanned deviation from an optimum constant basic magnetic field can, on average, be strongly compensated, in particular more completely compensated, over all sections compared to using conventional methods, in particular slices, of the examination region. A high image quality of the magnetic resonance image data acquired in this way thus can be achieved due to the particularly high level of homogeneity in the basic magnetic field, in particular on average over the entire examination region. For example, artifacts in the magnetic resonance image data due to inhomogeneities in the basic magnetic field can be reduced or largely avoided.

In conventional dynamic shimming methods, the multiple first shim parameter sets and the second shim parameter sets are ascertained independently of each other. By contrast, in accordance with the invention, consideration of the multiple first shim parameter sets when ascertaining the second shim parameter set includes a consideration of field contributions of the multiple first shim parameter sets.

This results in the advantage that a virtual basic magnetic field, which has already been corrected by multiple first shim parameter sets, has a higher homogeneity and/or a lower variation than a basic magnetic field that actually physically exists before a dynamic shimming process. For a virtual basic magnetic field of this kind that has been corrected by the multiple first shim parameter sets, a second shim parameter set can usually be ascertained for the at least one static second shim channel more easily and/or more preferably, such that, after taking into account field contributions of dynamic shimming by the at least one first shim channel, residual inhomogeneities in the basic magnetic field can be compensated more completely across the entire examination region. A variation in the basic magnetic field within the individual sections of the examination region then can be reduced following adjustment of the at least one second shim channel and dynamic adjustment of the at least one first shim channel for the respective sections.

In an embodiment, the first shim channel volume and the second shim channel volume are disjunct. In this way, in particular, each shim channel of the shim arrangement belongs either only to the first shim channel volume or only to the second shim channel volume. The shim parameter sets therefore can be calculated separately for the at least one first shim channel of the first shim channel volume, and for the at least one second shim channel of the second shim channel volume.

In another embodiment, before ascertaining the multiple first shim parameter sets, a first B0 field map is acquired, and the multiple first shim parameter sets are ascertained using the first B0 field map. Acquiring the first B0 field map can be done by scanning the first B0 field map, by a method known to those skilled in the art. A B0 field map is a field distribution of the basic magnetic field of the magnetic resonance scanner. The B0 field map is proportional to the basic magnetic field (B0 field) of the magnetic resonance scanner. This B0 field map will now be called a first B0 field map. The B0 field map can be used to identify inhomogeneities in the basic magnetic field that occur when the examination object is positioned in the magnetic resonance scanner. The multiple first shim parameter sets can then be ascertained using the first B0 field map such that the inhomogeneities in the basic magnetic field can be at least partially compensated by means of the multiple first shim parameter sets applied to the at least one first shim channel during acquisition of the magnetic resonance image data. The inhomogeneities in the basic magnetic field are compensated specifically for the first section and the second section of the examination region. In this way the first B0 field map constitutes an advantageous starting point for ascertaining the plurality of first shim parameter sets.

In another embodiment, a second B0 field map is calculated using the first B0 field map and the multiple first shim parameter sets, and the multiple first shim parameter sets are taken into account when ascertaining the second shim parameter set such that the second shim parameter set is ascertained using the second B0 field map. The multiple first shim parameter sets are therefore taken into account indirectly when ascertaining the second shim parameter set, namely via the second B0 field map calculated using the multiple first shim parameter sets. The second B0 field map can be calculated using the first B0 field map and the multiple first shim parameter sets, for example as described below, but by means of a different approach that is considered expedient to those skilled in the art. The multiple first shim parameter sets can be taken into account particularly advantageously when ascertaining the second shim parameter set via the calculated second B0 field map.

In another embodiment, the second B0 field map is calculated using the first B0 field map and the multiple first shim parameter sets such that B0 field contributions, resulting from the plurality of first shim parameter sets, are offset against the first B0 field map. The B0 field contributions of the respective shim parameter sets are preferably offset separately for the sections. A first spatial section of the second B0 field map is calculated using the first spatial section of the first B0 field map and the first shim parameter set, which is ascertained for the first section, with a first spatial section of the B0 field map being generated, and a second spatial section of the second B0 field map is calculated using the second section of the first B0 field map and the first shim parameter set, which is determined for the second spatial section, with a second spatial section of the second B0 field map being generated. In this way the second shim parameter set can be ascertained using the second B0 field map. Following mathematical removal of the B0 field contributions of the multiple first shim parameter sets from the first B0 field map, the second B0 field map can constitute an advantageous starting point for ascertaining the second shim parameter set. In this way the second shim parameter set can particularly advantageously compensate the inhomogeneities in the basic magnetic field that remain following consideration of the plurality of first shim parameter sets.

In another embodiment, a spatial portion of the first B0 field map is offset against the B0 field contributions, resulting from an appropriate first shim parameter set of the plurality of first shim parameter sets, wherein the appropriate first shim parameter set has been specifically ascertained for the section of the multiple sections that corresponds to the spatial portion. In this way the B0 field contributions are advantageously taken into account separately for different first shim parameter sets of the multiple first shim parameter sets when ascertaining the second shim parameter set.

In another embodiment, a third B0 field map is calculated using the first B0 field map and the second shim parameter set, wherein multiple adjusted first shim parameter sets is ascertained for the at least one first shim channel using the third B0 field map, and the at least one first shim channel is adjusted, using the multiple adjusted first shim parameter sets, for ascertaining the magnetic resonance image data. The second B0 field map can be adjusted using the second shim parameter set such that B0 field contributions, resulting from the second shim parameter set, are offset against the first B0 field map. In this way it is not the original number of first shim parameter sets ascertained on the basis of the first B0 field map, but rather the adjusted multiple first shim parameter sets again ascertained on the basis of the third B0 field map that are set when acquiring the magnetic resonance image data for the at least one first shim channel. The multiple adjusted first shim parameter sets can compensate the inhomogeneities in the basic magnetic field that exist for the plurality of sections of the examination region even better than the multiple first shim parameter sets. One reason for this is that the compensation fields induced by the at least one second shim channel can in this way be taken into account specifically, and not just globally, for the multiple sections of the examination region. No additional scanning time is required for this, since the third B0 field map can be calculated from the first B0 field map that has already been scanned.

In another embodiment, in order to acquire the magnetic resonance image data, first the at least one second shim channel is adjusted using the second shim parameter set, then the at least one first shim channel is adjusted using a first shim parameter set, which is ascertained for a first section of the multiple sections. Therefore, magnetic resonance image data are acquired from the first section, then the at least one first shim channel is adjusted using a first shim parameter set, which is ascertained for a second section of the multiple sections, then magnetic resonance image data are acquired from the second section. The at least one second shim channel is adjusted in this way, in particular for acquisition of the magnetic resonance image data from the first section and the second section using the second shim parameter set. The at least one first shim channel is adjusted, for acquisition of the magnetic resonance image data using the first shim parameter set that was ascertained for the first section. In particular the at least one first shim channel is adjusted using the first shim parameter set ascertained for the second section for ascertaining magnetic resonance image data from the second section. In this way inhomogeneities in the basic magnetic field can be compensated for the different sections of the examination region.

In another embodiment, a second settling time elapses between adjustment of the at least one second shim channel and acquisition of the magnetic resonance image data from the first section, and a first settling time elapses between adjustment of the at least one first shim channel using the first shim parameter set and acquisition of the magnetic resonance image data from the first section. The first settling time is shorter than the second settling time. The settling time is the time that elapses between adjusting a shim channel with a current and adjusting a desired field contribution of the shim channel. The at least one first shim channel can be adjusted more quickly than the at least one second shim channel in this way. The at least one first shim channel thus can be adjusted dynamically.

In another embodiment, after adjusting the at least one second shim channel, a fourth B0 field map is acquired, and multiple altered first shim parameter sets are acquired for the at least one first shim channel using the fourth B0 field map. During acquisition of the magnetic resonance image data, the at least one first shim channel is adjusted using these multiple altered first shim parameter sets. The additional scanning time for acquiring the fourth B0 field map can be worthwhile if the compensation fields actually induced by the at least one second shim channel differ from theoretical and/or calculated compensation fields (see calculation of the third B0 field map in the paragraph preceding the penultimate paragraph one above).

In another embodiment, the first B0 field map is acquired using raw data representing at least three echo signals that are each acquired following an excitation of the examination region. The fourth B0 field map can also be acquired in this way. A specific choice of the echo time difference between the first and last echo signals means that the B0 field maps that are calculated from phase-differential images of the first and last echo signal depend only on the local B0 deviation, and not on the spectral composition of the tissue. The B0 map calculated from the phase difference of the first and last echo signals can then be unwrapped, i.e. phase envelopes as a consequence of the $2\pi$ periodicity of the phase can be mathematically removed. The signals of the intermediate echoes can be used, inter alia, for an absolute calibration of the unwrapped B0 field map. As a result, a B0 field map can be calculated in which each pixel value is proportional to the local absolute deviation from the resonance frequency. This has the advantage that the RF center frequency (shim channel of the $0^{th}$ order) can also be directly determined from the B0 field map. A separate frequency adjustment within the respective sections thus can be omitted.

The inventive magnetic resonance apparatus has a canner with a shim arrangement having a first shim channel volume having at least one first shim channel and a second shim channel volume having at least one second shim channel, and a computer having a division processor, a first ascertaining processor and a second ascertaining processor, wherein the magnetic resonance apparatus is designed to implement the inventive method.

In this way the magnetic resonance apparatus is designed to carry out a method for magnetic resonance imaging in an examination region of an examination object. The division processor is configured to divide the examination region into multiple sections. The first ascertaining processor is configured to ascertain multiple first shim parameter sets for the at least one first shim channel, wherein one first shim parameter among the multiple first shim parameter sets is ascertained respectively for the multiple sections. The second ascertaining processor is configured to ascertain a second shim parameter set for the at least one second shim channel by taking into account the multiple first ascertained shim parameter sets. The image data acquisition scanner is designed to acquire magnetic resonance image data of the examination region of the examination object, wherein, before acquiring the magnetic resonance image data, the at least one second shim channel is adjusted using the second shim parameter set, and the at least one first shim channel for acquiring the magnetic resonance image data from a specific section of the multiple sections is adjusted using a first shim parameter set ascertained for the specific section.

In an embodiment of the magnetic resonance apparatus, the shim arrangement is configured to that the first shim channel volume and the second shim channel volume are disjunct.

In another embodiment of the magnetic resonance apparatus, the magnetic resonance apparatus has a field map acquisition unit, wherein the field map acquisition unit and the first ascertaining processor are designed such that, before ascertaining the multiple first shim parameter sets, a first B0 field map is acquired, and the multiple first shim parameter sets are ascertained using the first B0 field map.

In another embodiment of the magnetic resonance apparatus, the magnetic resonance apparatus has a field map acquisition unit, wherein the field map acquisition unit, the first ascertaining processor and the second ascertaining processor are designed such that a second B0 field map is calculated using the first B0 field map and the multiple first shim parameter sets, and the multiple first shim parameter sets are taken into account when ascertaining the second shim parameter set such that the second shim parameter set is ascertained using the second B0 field map.

In another embodiment of the magnetic resonance apparatus, the magnetic resonance apparatus has a field map acquisition unit, wherein the field map acquisition unit is designed such that the second B0 field map is calculated using a first B0 field map and the multiple first shim parameter sets, such that B0 field contributions, resulting from the multiple first shim parameter sets, are offset against the first B0 field map.

In another embodiment of the magnetic resonance apparatus, the magnetic resonance apparatus has a field map acquisition unit, wherein the field map acquisition unit is designed such that a spatial portion of the first B0 field map is offset against the B0 field contributions, resulting from an appropriate first shim parameter set of the multiple first shim parameter sets, wherein the appropriate first shim parameter set has been specifically ascertained for the section of the multiple sections that corresponds to the spatial portion.

In another embodiment of the magnetic resonance apparatus, the magnetic resonance apparatus has a field map acquisition scanner, wherein the image data acquisition processor, the first ascertaining processor and the field map acquisition scanner are designed such that a third B0 field map is calculated using the first B0 field map and the second shim parameter set, and multiple adjusted first shim parameter sets are ascertained for the at least one first shim channel using the third B0 field map. For acquiring the magnetic resonance image data, the at least one first shim channel is adjusted using the multiple adjusted first shim parameter sets.

In another embodiment of the magnetic resonance apparatus, the image data acquisition scanner is operated such that, for acquiring the magnetic resonance image data, first the at least one second shim channel is adjusted using the second shim parameter set, then the at least one first shim channel is adjusted using a first shim parameter set, which is ascertained for a first section of the multiple sections. Then magnetic resonance image data are acquired from the first section, then the at least one first shim channel is adjusted using a first shim parameter set, which is ascertained for a second section of the multiple sections, then magnetic resonance image data are acquired from the second section.

In another embodiment of the magnetic resonance apparatus, the image data acquisition scanner is operated such that a second settling time elapses between adjusting the at least one second shim channel and acquiring the magnetic resonance image data from the first section, and a first settling time elapses between adjusting the at least one first shim channel using the first shim parameter set and acquiring the magnetic resonance image data from the first section. The first settling time is shorter than the second settling time.

In another embodiment of the magnetic resonance apparatus, the magnetic resonance apparatus has a field map acquisition unit, wherein the field map acquisition unit and the image data acquisition scanner are designed such that, after adjusting the at least one second shim channel, a fourth B0 field map is acquired, and multiple altered first shim parameter sets are ascertained for the at least one first shim channel using the fourth B0 field map. During acquisition of the magnetic resonance image data, the at least one first shim channel is adjusted using the multiple altered first shim parameter sets.

In another embodiment of the magnetic resonance apparatus, the magnetic resonance apparatus has a field map acquisition unit, wherein the field map acquisition unit is designed such that the first B0 field map is acquired using raw data, representing at least three echo signals that are each acquired following an excitation of the examination region.

The invention also encompasses a non-transitory, computer-readable data storage medium that can be loaded directly into a memory of a programmable control computer of a magnetic resonance apparatus and that is encoded with program code to carry out the inventive method when the program code is executed in the control computer of the magnetic resonance apparatus. The inventive method can consequently be carried out quickly, robustly and in a manner that can be repeated in an identical manner. The control computer must have the components, such as an appropriate main memory, an appropriate graphics card or an appropriate logic unit, so the respective method steps can be carried out efficiently.

Examples of electronically readable data carriers are a DVD, magnetic tape or a USB stick, on which electronically readable control information, in particular software.

The advantages of the inventive magnetic resonance apparatus and of the inventive data storage medium essentially correspond to the advantages of the inventive method, which have been described above in detail. Features, advantages or alternative embodiments mentioned in this connection are similarly applicable to the other aspects of the invention. The functional features of the method are formed by appropriate physical modules, in particular by hardware modules.

DESCRIPTION OF THE PREFERRED EMBODIMENTS

Figure 1:
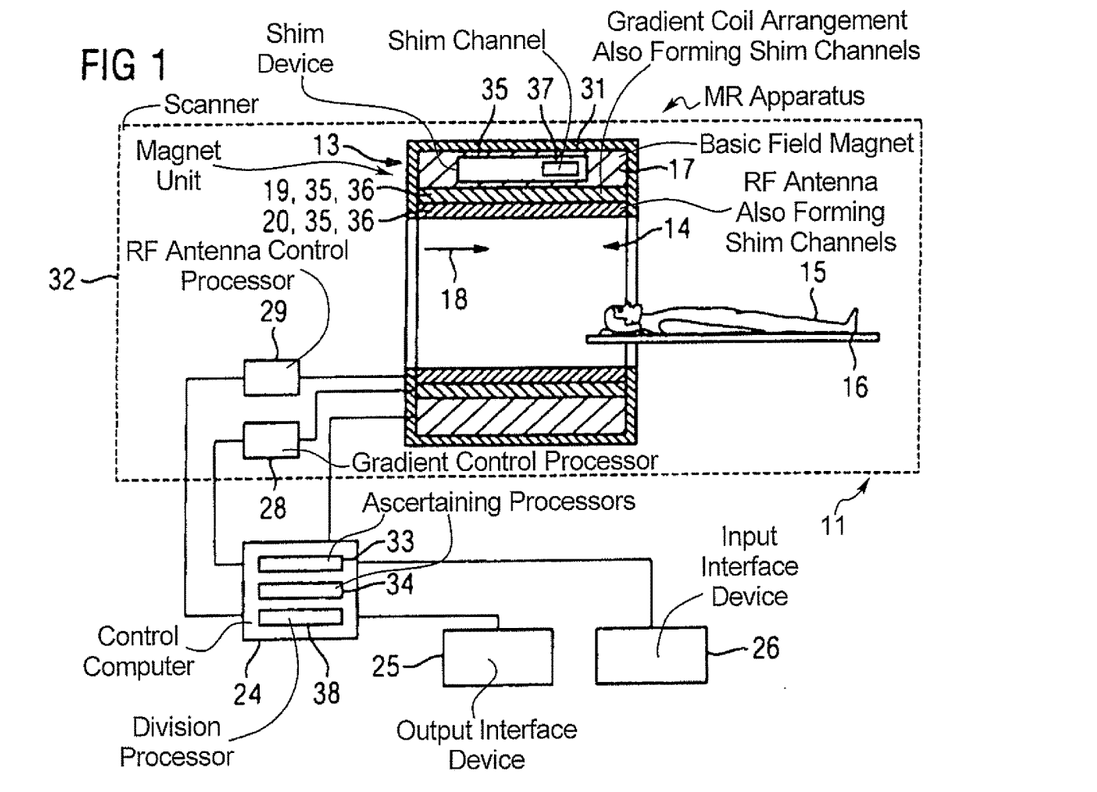
FIG. 1 schematically illustrates an inventive magnetic resonance apparatus.

FIG. 1 schematically shows an inventive magnetic resonance apparatus 11. The magnetic resonance apparatus 11 has a data acquisition scanner that includes a magnet unit 13, having a basic field magnet 17 that generates a strong, constant basic magnetic field 18. The scanner 32 has a cylindrical patient-receiving region 14 for receiving an examination object 15, in the present case a patient, with the patient-receiving region 14 being cylindrically surrounded in a circumferential direction by the magnet unit 13. The patient 15 can be moved by a patient-positioning device 16 of the magnetic resonance apparatus 11 into the patient-receiving region 14. The patient-positioning device 16 has for this purpose an examination table arranged so as to move inside the scanner 32. The magnet unit 13 is shielded from the outside by a housing shell 31.

The scanner 32 also has a gradient coil arrangement 19 that generates magnetic field gradients that are used for spatial encoding during imaging. The gradient coil arrangement 19 is controlled by a gradient control processor 28. The scanner 32 also has a radio-frequency antenna 20, which is designed in the illustrated case as a body coil permanently integrated in the scanner 32, and a radio-frequency antenna control processor 29 that operates the antenna 20 so as to excite nuclear spins in the object 15 so as to cause the excited nuclear spins to deviate from the polarization that is established in the basic magnetic field 18 generated by the basic field magnet 17. The radio-frequency antenna unit 20 is controlled by the radio-frequency antenna control processor 29 and to radiate radio-frequency magnetic resonance sequences into an examination space that is essentially formed by the patient-receiving region 14. The radio-frequency antenna unit 20 is also designed to receive magnetic resonance signals, in particular from the patient 15 that occur as the excited nuclear spins relax.

For controlling the basic field magnet 17, the gradient control processor 28 and the radio-frequency antenna control processor 29, the magnetic resonance apparatus 11 has a control computer 24. The control computer 24 centrally controls the magnetic resonance apparatus 11, such as, to carry out a predetermined imaging gradient echo sequence. Control information, such as imaging parameters, and reconstructed magnetic resonance images, can be supplied for a user at an output interface device 25, in the present case a display monitor, of the magnetic resonance apparatus 11. Furthermore, the magnetic resonance apparatus 11 has an input interface device 26, via which a user can enter information and/or parameters during a scanning process. The control computer 24 can include the gradient control processor 28 and/or radio-frequency antenna control processor 29 and/or the output interface device 25 and/or the input interface device 26. In the illustrated case the control computer 24 has a division processor 38, a first ascertaining processor 33 and a second ascertaining processor 34. These processors can be separate from each other or combined.

The scanner also has a shim device 35, having a first shim channel volume having at least one first shim channel 36, and a second shim channel volume having at least one second shim channel 37.

The first shim channel volume includes, for example, three shim channels 36. In the case illustrated in FIG. 1, the three first shim channels 36 are formed by the three gradient coils of the gradient coil arrangement 19. These three first shim channels 36 generate shim fields in the x-direction, y-direction and in the z-direction. As an example, the x-direction proceeds along a horizontal body axis of the examination object 15 lying on his or her back, the y-direction proceeds along the vertical body axis of the examination object 15, and the z-direction proceeds along a sagittal axis of the examination object 15. For different reasons, the gradient coils and their gradient amplifiers are designed such that the gradient fields can be varied (switched) on a timescale of a few microseconds. In other words, this time is short compared to the time that elapses between acquisition of data from different sections and/or slices of an examination region. The three first shim channels 36 of the first order thus can be used for dynamic shimming. The first shim channel volume also has an RF center frequency. This RF center frequency reproduces the mean deviation of the resonance frequency within the section, to which the respective first shim parameter set is allocated, from the RF center frequency that was adjusted during acquisition of the first B0 field map. The RF center frequency can be formally treated like a shim channel, namely a shim channel of the $0^{th}$ order.

The second shim channel volume has, for example, five dedicated second shim channels 37. These five second shim channels 37 can generate shim fields of the second order. These shim fields are proportional to the current flowing through the second shim channels 37 and the spatial characteristic of the shim fields can be described, for example, in a good approximation by $z^2-(x^2+y^2)/2$, xz, yz, $(x^2-y^2)/2$ and xy. The amplifiers associated with the second shim channels 37 are designed such that a settling time in the order of one second or longer elapses between the change in the current through the second shim channel 37 and the adjustment of the desired field. This settling time is longer than the typical time between acquisition of data from different sections and/or slices of an examination region. The five second shim channels 37 of the second order thus cannot typically be used for dynamic shimming. Of course the second shim channels 37 can also include shim channels of a higher order, which generate, for example, shim fields of a third or fourth order. The first shim channel volume and the second shim channel volume are disjunct in the illustrated case.

The magnetic resonance apparatus 11 is designed, together with the image data acquisition scanner 32, the control computer 24 and shim arrangement 35 to implement the inventive method for magnetic resonance imaging.

The illustrated magnetic resonance apparatus 11 can of course have further components that magnetic resonance apparatuses conventionally have. The general operation of a magnetic resonance apparatus is known to those skilled in the art, moreover, so a detailed description of the further components is not necessary herein.

Figure 2:
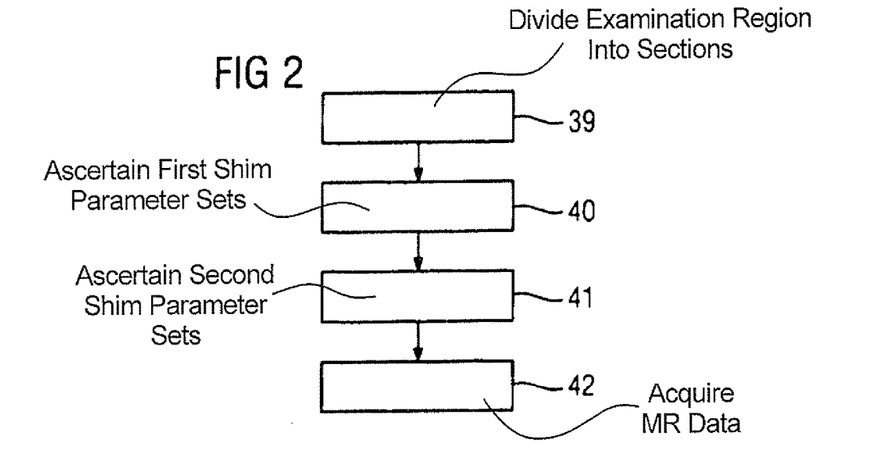
FIG. 2 is a flowchart of a first embodiment of the inventive method.

FIG. 2 is a flowchart of a first embodiment of an inventive method for magnetic resonance imaging in an examination region of an examination object 15 by operation of the magnetic resonance apparatus 11 in particular the scanner 32 and shim unit 35 thereof.

In a first method step 39, the examination region is divided into a plurality of sections by the division processor 38. For example, each excitation slice of a slice stack forms a section of the plurality of sections.

In a further method step 40, a number of first shim parameter sets is ascertained for the at least one first shim channel 36, wherein one first shim parameter set respectively of the multiple first shim parameter sets is ascertained respectively for the multiple sections by the first ascertaining processor 33.

In a further method step 41, a number of second shim parameter sets is ascertained for the at least one second shim channel 37 by taking into account the multiple first ascertained shim parameter sets, by the second ascertaining processor 34.

In a further method step 42, magnetic resonance image data of the examination region of the examination object 15 are acquired by operation of the image data acquisition scanner 32, wherein, before acquisition of the magnetic resonance image data, the at least one second shim channel 37 is adjusted using the second shim parameter set, and the at least one first shim channel 36 is adjusted for acquiring the magnetic resonance image data from a specific section of the multiple sections using a first shim parameter set ascertained for the specific section.

The acquired magnetic resonance image data can be presented on the display monitor of the output interface device 25 and/or stored in a database.

Figure 3:
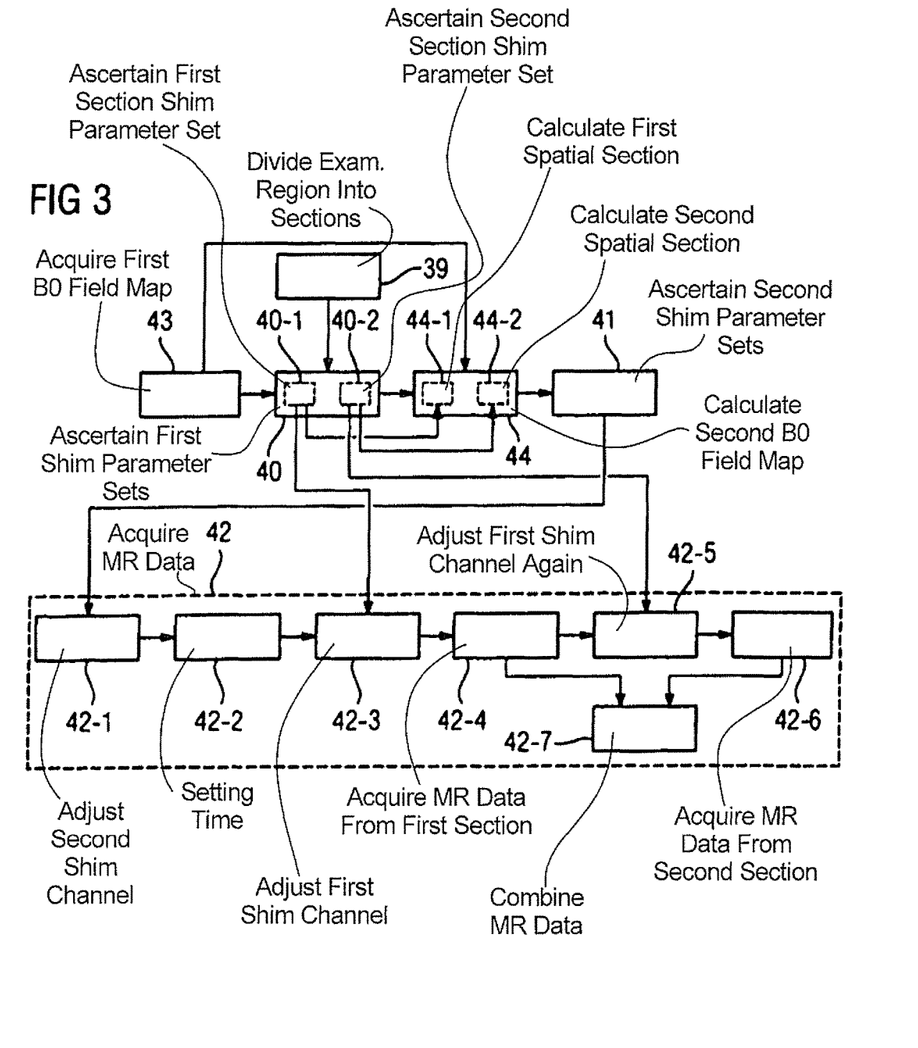
FIG. 3 is a flowchart of a second embodiment of the inventive method.

FIG. 3 is a flowchart of a second embodiment of the inventive method for magnetic resonance imaging in an examination region of an examination object 15 by operation of the magnetic resonance apparatus 11.

The following description is essentially limited to the differences from the exemplary embodiment in FIG. 2, with reference being made with respect to unchanging method steps to the description of the exemplary embodiment in FIG. 2. Method steps that essentially stay the same are basically numbered with the same reference numerals.

The embodiment of the inventive method shown in FIG. 3 essentially includes method steps 39, 40, 41, 42 of the first embodiment of the inventive method according to FIG. 2. The embodiment of the inventive method shown in FIG. 3 has additional method steps and substeps. An alternative method sequence to FIG. 3 is also conceivable that has just some of the additional method steps and/or substeps shown in FIG. 2. Of course an alternative method sequence to FIG. 3 can also have additional method steps and/or substeps.

In the example of FIG. 3 it is assumed for a better overview that the examination region is divided into two sections in the first method step 39, i.e., for example, two individual slices. The concept may of course be arbitrarily expanded to a division into more sections.

In a further method step 43 a first B0 field map is acquired before ascertaining the plurality of first shim parameter sets. The first B0 field map reproduces local deviations from an ideal constant basic magnetic field 18 within the multiple sections of the examination region. The B0 field map can be a frequency map that reproduces a local deviation of a resonance frequency from a system frequency. A frequency map $\Delta f(x,y,z)$ and a B0 field map $\Delta B_0(x,y,z)$ may typically be converted such that:

$$\Delta f(x,y,z) = (\gamma/(2\pi)) \times \Delta B_0(x,y,z)$$

Here $\gamma/(2\pi)$ is the gyromagnetic ratio, which for protons is 42.576 MHz/T.

The plurality of first shim parameter sets is ascertained in a further method step 40 using the first B0 field map. In a first substep 40-1 of the further method step 40 a first section shim parameter set is ascertained using the first B0 field map and in a second substep 40-2 of the further method step 40 a second section shim parameter set is ascertained using the first B0 field map. The first section shim parameter set is, in particular, a first shim parameter set that has been ascertained for the first section. The second section shim parameter set is a first shim parameter set that has been ascertained for the second section. Of course further section shim data sets can also be ascertained. In particular, a section shim parameter set can be ascertained for each slice of the examination region.

The first shim parameter set, which was ascertained for the first section, $\Delta f_0^{(1)}$, $\Delta G_x^{(1)}$, $\Delta G_y^{(1)}$, $\Delta G_z^{(1)}$ has a first resonance frequency $\Delta f_0^{(1)}$ for the frequency adjustment, a first x-gradient offset current $\Delta G_x^{(1)}$ for the gradient coil in the x-direction, a first-y-gradient offset current $\Delta G_y^{(1)}$ for the gradient coil in the y-direction and a first z-gradient offset current $\Delta G_z^{(1)}$ for the gradient coil in the z-direction. The first shim parameter set, which was ascertained for the first section, $\Delta f_0^{(1)}$, $\Delta G_x^{(1)}$, $\Delta G_y^{(1)}$, $\Delta G_z^{(1)}$ is advantageously chosen such that local field deviations $\Delta B_0(x,y,z)$ in the first section are optimally compensated.

The first shim parameter set, which was ascertained for the second section, $\Delta f_0^{(2)}$, $\Delta G_x^{(2)}$, $\Delta G_y^{(2)}$, $\Delta G_z^{(2)}$ comprises, in particular, a second resonance frequency $\Delta f_0^{(2)}$ for the frequency adjustment, a second x-gradient offset current $\Delta G_x^{(2)}$ for the gradient coil in the x-direction, a second y-gradient offset current $\Delta G_y^{(2)}$ for the gradient coil in the y-direction and a second z-gradient offset current $\Delta G_z^{(2)}$ for the gradient coil in the z-direction. The first shim parameter set, which was ascertained for the second section, $\Delta f_0^{(2)}$, $\Delta G_x^{(2)}$, $\Delta G_y^{(2)}$, $\Delta G_z^{(2)}$ is advantageously chosen such that local field deviations $\Delta B_0(x,y,z)$ in the second section are optimally compensated.

To ascertain the shim parameter sets for the first and/or second section an equation with the following form can be deployed for each pixel of the first B0 field map within the first section and/or the second section:

$$-\Delta B_o(x, y, z) = \frac{2\pi}{\gamma}\Delta f_0 + \Delta G_x(x - x_0) + \Delta G_y(y - y_0) + \Delta G_z(z - z_0)$$

wherein (x,y,z) is the coordinate of the respective pixel, (x0,y0,z0) the coordinate of an isocenter of the gradient coil arrangement 19 within the first B0 field map. The isocenter is the location at which the field contribution of the gradient coil arrangement 19 is zero. $\Delta G_x$ indicates a change in the gradient field in the x-direction of the first B0 field map with respect to the adjustment during acquisition of the B0 field map. Accordingly, $\Delta G_y$ and $\Delta G_z$ indicate a change in the gradient field in the y and z-directions respectively of the B0 field map with respect to the corresponding adjustment during acquisition of the B0 field map. $\Delta f_0$ indicates a change in an RF center frequency with respect to the adjustment during acquisition of the B0 field map.

As a whole, these equations form an overdetermined linear equation system for each section of the examination region, and this can be solved using standard methods. The four unknowns $\Delta f_0^{(1)}$, $\Delta G_x^{(1)}$, $\Delta G_y^{(1)}$, $\Delta G_z^{(1)}$ of the first shim parameter set for the first section or $\Delta f_0^{(2)}$, $\Delta G_x^{(2)}$, $\Delta G_y^{(2)}$, $\Delta G_z^{(2)}$ of the first shim parameter set for the second section therefore can each be ascertained. If creation of the B0 field map is based on the scan of the phase difference between acquired MR images with a different echo time then no information about the local B0 field deviation can be obtained from pixels that essentially contain only noise. Pixels of this kind should therefore be excluded from the solution to the equation systems. This can occur by way of background segmenting and/or weighting of the individual equations proportionally to the pixel value of a magnitude image at the location (x,y,z). The magnitude image can likewise be extracted from the magnetic resonance scan data that is acquired in order to create the first B0 field map.

In a further method step 44 a second B0 field map is calculated using the first B0 field map and using the plurality of first shim parameter sets. The second B0 field map is calculated using the first B0 field map and using the plurality of first shim parameter sets such that B0 field contributions, resulting from the plurality of first shim parameter sets, are offset against the first B0 field map. Here, in particular, a spatial section of the first B0 field map is offset against the B0 field contributions, resulting from an appropriate suitable first shim parameter set of the plurality of first shim parameter sets, with the appropriate first shim parameter set having been specifically ascertained for the section of the plurality of sections that corresponds to the spatial section.

In the illustrated case a first spatial section of the second B0 field map is calculated in a first substep 44-1 of the further method step 44 using the first spatial section of the first B0 field map and the first shim parameter set ascertained for the first section. In a second substep 44-2 of the further method step 44 a second spatial section of the second B0 field map is calculated using the second spatial section of the first B0 field map and the first shim parameter set ascertained for the second section. The second B0 field map then comprises the two ascertained spatial sections.

To calculate the second B0 field map the B0 field contributions of the first shim parameter set ascertained for the respective section for the at least one first shim channel 36 are added to the first B0 field map pixel-by-pixel, for example for each section. This means that the second B0 field map represents a new virtual B0 field map $\Delta B_0'(x,y,z)$, to which the following applies:

$$\Delta B_0'(x, y, z) = \Delta B_o(x, y, z) +$$
$$\begin{cases} \frac{2\pi}{\gamma}\Delta f_0^{(1)} + \Delta G_x^{(1)}(x-x_0) + \Delta G_y^{(1)}(y-y_0) + \Delta G_z^{(1)}(z-z_0), \text{ if } (x,y,z) \in V1 \\ \frac{2\pi}{\gamma}\Delta f_0^{(2)} + \Delta G_x^{(2)}(x-x_0) + \Delta G_y^{(2)}(y-y_0) + \Delta G_z^{(2)}(z-z_0), \text{ if } (x,y,z) \in V2 \end{cases}$$

Therein V1 denotes the first section, V2 the second section and the element sign from the set theory here represents "the pixel considered having coordinates (x,y,z) belongs to the first section V1 or to the second section V2". The second (virtual) B0 field map $\Delta B_0'(x,y,z)$ will, generally, have lower B0 field deviations than the original scanned first B0 field map $\Delta B_0(x,y,z)$. Locally within a section the second B0 field map can approximately reproduce the B0 field characteristic following adjustment of the at least one first shim channel 37 using the respective first shim parameter sets.

In further method step 41, ascertaining the second shim parameter set, the plurality of first shim parameter sets is taken into account when ascertaining the second shim parameter set such that the second shim parameter set is ascertained using the second B0 field map. The second shim parameter set is advantageously ascertained such that the B0 field reproduced by the second B0 field map $\Delta B_0'(x,y,z)$ is optimally compensated.

The field contribution $\Delta B_j(x,y,z)$ of the $j^{th}$ shim channel of the at least one second shim channel 37 at location (x,y,z) is proportional to the shim current $I_j$ in the $j^{th}$ shim channel:

$$\Delta B_j(x,y,z) = C_j(x,y,z) \cdot P_j \cdot I_j$$

$C_j(x,y,z)$ is the known standardized field distribution of the second shim channel j and $P_j$ the likewise known location-independent sensitivity of the second shim channel j. The index j assumes values of 1, ..., N2, where N2 is the number of second shim channels 37. To ascertain the unknown shim currents $I_1$, ..., $I_{N2}$ an equation with the following form can be deployed for each pixel in the examination region:

$$-\Delta B_0'(x, y, z) = \frac{2\pi}{\gamma}\Delta f_0 + \sum_{j=1}^{N2} \Delta B_j(x, y, z) = \frac{2\pi}{\gamma}\Delta f_0 + \sum_{j=1}^{N2} C_j(x, y, z) \cdot P_j \cdot \Delta I_j$$

The examination region is here intended to mean the combined volume of the two sections. As a whole said equations therefore again form an overdetermined linear equation system: overdetermined because the number of pixels in the examination region is generally very much greater than the number of unknowns. The sought unknowns in this equation system are the N2 values $\Delta I_j$ which indicate the change in the current in the $j^{th}$ shim channel compared to the adjustment during acquisition of the first B0 field map, and again a term $\Delta f_0$ without location dependency. The overdetermined equation system can be solved, for example, within the sense of the smallest quadratic deviation using standard methods. The result of step 41 is therefore a second shim parameter set $\Delta f_0$, $I_1$, ..., $I_{N2}$, for adjustment of the at least one second shim channel 37.

The magnetic resonance image data are typically acquired in further method step 42 in a nested 2D multi-slice scan. The number of slices can typically be between 5 and 50. Each of these slices can have a thickness of typically 2 mm to 10 mm. The field of view of a slice is typically between 200×200 mm² (for example in the case of an axial head examination) and 400×400 mm² (for example in the case of an abdominal examination). As a rule, the slices are oriented parallel to each other with a gap of 0 to 50 percent of the slice thickness between adjacent slices. Each of these slices and/or a section of each slice can represent a section of the examination region. In the illustrated case there are only two sections of the examination region for the sake of clarity, however. The time between acquisition of data of different slices is TR/N, where TR is the repetition time and N the number of slices from which data is acquired in a repetition interval. The repetition time TR indicates the time between successive excitations of a specific slice. Depending on the underlying sequence technique, the TR time lies between a few ms and a few seconds. The time between acquisition of data from different slices is accordingly reduced by a factor N. The parameters described here are only examples. The magnetic resonance image data can also be acquired in further method step 42 using different scanning parameters to those described.

Acquiring the magnetic resonance image data in further method step 42 has a first substep 42-1 in which firstly the at least one second shim channel 37 is adjusted using the second shim parameter set. For example, the five second shim channels 37 are adjusted using the shim currents $I_1, \ldots, I_5$.

In a second substep 42-2 of the further method step 42 a second settling time elapses between adjustment of the at least one second shim channel 37 and acquisition of the magnetic resonance image data from the first section in a fourth substep 42-4. This second settling time is longer than a first settling time which elapses between adjustment of the at least one first shim channel 36 using the first shim parameter set, which was ascertained for the first section, and acquisition of the magnetic resonance image data from the first section. The settling time is waited for until the actual field contribution of the at least one second shim channel 37 matches the calculated field contribution.

In a third substep 42-3 of further method step 42 the at least one first shim channel 36 is then adjusted using the first shim parameter set which was ascertained for the first section. In the example the gradient offset currents $\Delta G_x^{(1)}$, $\Delta G_y^{(1)}$, $\Delta G_z^{(1)}$ are therefore added to the gradient offset currents which were adjusted during acquisition of the first B0 field map. Furthermore, the RF enter frequency can be changed by $\Delta f_0^{(1)} + \Delta f_0$ with respect to the value during acquisition of the first B0 field map. Here $\Delta f_0^{(1)}$ is the change in center frequency ascertained in step M3 for the first section and $\Delta f_0$ is the constant term without location dependency from the second shim parameter set.

In a fourth substep 42-4 of the further method step 42 magnetic resonance image data is then acquired from the first section. The at least one first shim channel 36 remains adjusted for acquisition of the magnetic resonance image data from the first section using the first shim parameter set which was ascertained for the first section.

In a fifth substep 42-5 of the further method step 42 the at least one first shim channel 36 is then adjusted using the first shim parameter set which was ascertained for the second section. For this purpose the gradient offset currents $\Delta G_x^{(2)}$, $\Delta G_y^{(2)}$, $\Delta G_z^{(2)}$ are added to the gradient offset currents which were adjusted during acquisition of the first B0 field map. Adjustment of the RF center frequency is changed by $\Delta f_0^{(2)} + \Delta f_0$ with respect to the adjustment during acquisition of the first B0 field map.

It should be noted in this connection that when adjusting the at least one first shim channel 36 for a specific section only the adjustments between transmitting and receiving paths of the magnetic resonance sequence can be active. Whether, for example, the gradient offset currents are switched on before a first radio-frequency excitation pulse within a section or, for example, only with a slice selection gradient of the first radio-frequency excitation pulse, is irrelevant if physical effects as a consequence of the altered gradient current are not taken into account. Due to unavoidable eddy currents as a consequence of the altered gradient current, which decay exponentially with a typical time constant, it can be expedient to adjust the at least one first shim channel 36 using the shim parameter sets as early as possible without extending the total scanning time.

In a sixth substep 42-6 of further method step 42 magnetic resonance image data are then acquired from the second section. The at least one first shim channel 36 remains adjusted for acquisition of the magnetic resonance image data from the second section using the first shim parameter set which was ascertained for the second section.

The method steps 42-3 to 42-6 can be repeated until all magnetic resonance data is acquired from the two sections which is necessary for reconstruction of the images.

In a seventh substep 42-7 of the further method step 42 the magnetic resonance image data, which map the first section, and the magnetic resonance image data, which map the second section, are combined to form an overall magnetic resonance image data set. Magnetic resonance images from the two sections can then be reconstructed from this overall magnetic resonance image data set. The images can then be output, for example, on the display unit 25 and/or stored in a database.

Figure 4:
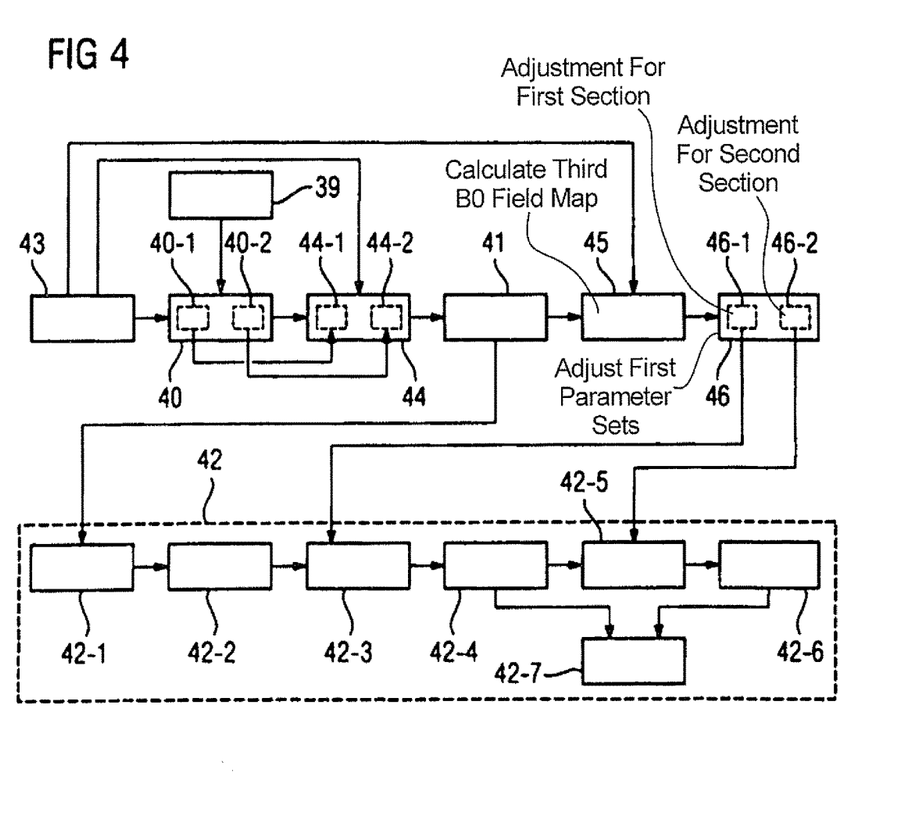
FIG. 4 is a flowchart of a third embodiment of the inventive method.

FIG. 4 is a flowchart of a third embodiment of the inventive method for magnetic resonance imaging in an examination region of an examination object 15 by means of a magnetic resonance apparatus 11.

The following description is essentially limited to the differences from the exemplary embodiment in FIG. 3, with reference being made in respect of unchanging method steps to the description of the exemplary embodiment in FIG. 3. Method steps that essentially stay the same are basically numbered with the same reference numerals.

In contrast to the approach shown in FIG. 3, the at least one first shim channel 36 is not adjusted during acquisition of the magnetic resonance image data in further method step 42 using the number of first shim parameter sets ascertained in further method step 40.

Instead, according to FIG. 4, a third B0 field map is calculated in a further method step 45 using the first B0 field map and the second shim parameter set. This can take account of the fact that the modified shim currents in the at least one second shim channel 37 influence the B0 field in the sections of the examination region. When calculating the first shim parameter sets of the at least one first shim channel 36 in further method step 40 this contribution is not initially taken into account. For this reason the known field contributions of the at least one second shim channel 37 are added to the original first B0 field map $\Delta B_0(x,y,z)$, with a third B0 field map $\Delta B_0''(x,y,z)$ being generated:

$$\Delta B_0''(x, y, z) = \Delta B_o(x, y, z) + \frac{2\pi}{\gamma}\Delta f_0 + \sum_{j=1}^{N2} \Delta C_j(x, y, z) \cdot P_j \cdot \Delta I_j$$

The new third B0 field map $\Delta B_0''(x,y,z)$ at least approximately reproduces (apart from the location-independent term $(2\pi/\gamma)\Delta f_0$) the field characteristic following adjustment of the at least one second shim channel 37.

In a further method step 46 a number of adjusted first shim parameter sets is then ascertained for the at least one first shim channel 36 using the third B0 field map. In a first substep 46-1 of the further method step 46 an adjusted first shim parameter set is therefore ascertained for the first section, and in a second substep 46-2 of the further method step 46 an adjusted second shim parameter set is ascertained for the second section. The result is a new set of shim adjustments $\Delta f_0'^{(1)}$, $\Delta G_x'^{(1)}$, $\Delta G_y'^{(1)}$, $\Delta G_z'^{(1)}$ for the first section and $\Delta f_0'^{(2)}$, $\Delta G_x'^{(2)}$, $\Delta G_y'^{(2)}$, $\Delta G_z'^{(2)}$ for the second section.

During acquisition of the magnetic resonance image data in further method step 42 the at least one first shim channel 36 is adjusted using the number of adjusted first shim parameter sets. In a third substep 42-3 of the further method step 42 the at least one first shim channel 36 is therefore adjusted for the first section using the adjusted first shim parameter set. In a fifth substep 42-5 of the further method step 42 the at least one first shim channel 37 is then adjusted for the second section using the adjusted second shim parameter set.

It should be noted that the adjusted first shim parameter sets and adjusted second shim parameter sets can also be ascertained iteratively. For this purpose, method steps 45, 46, 44, 41 are each performed in the given sequence in an $i^{th}$ iteration step. In method step 45 a B0"(i) field map is calculated using the first B0 field map and the second shim parameter set of the preceding iteration step. In method step 46 adjusted first shim parameter sets are calculated for the individual sections using the B0 field map B0"(i) calculated in respective method step 45. In method step 44 a further B0 field map B0'(i) is calculated using the B0"(i) field map (step 45) calculated in the respective iteration step and the adjusted first shim parameter sets for the individual sections ascertained respectively in method step 46. In method step 41 an adjusted second shim parameter set is in each case calculated on the basis of the B0 field map B0'(i) calculated in method step 41 of the $i^{th}$ iteration step. An abort criterion of the iterative method is if, compared to the adjusted first shim parameter set of the $(i-1)^{th}$ iteration step, the change in the adjusted first shim parameter sets of the $i^{th}$ step of each section is smaller for the corresponding section than a first threshold set predefined for the first shim channels and, compared to the second shim parameter set calculated in the $(i-1)^{th}$ step, the change in the second shim parameter set calculated in the $i^{th}$ iteration step is smaller than a second threshold set predefined for the second shim channels, or if a predefined maximum number of iteration steps is exceeded.

Figure 5:
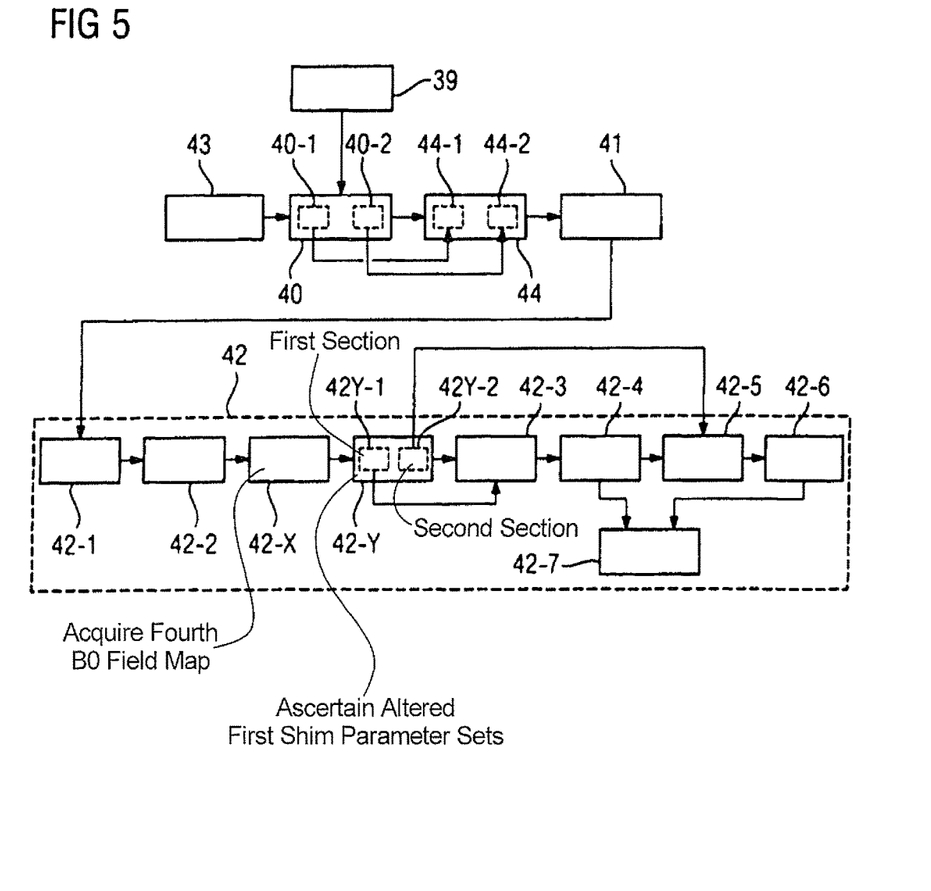
FIG. 5 is a flowchart of a fourth embodiment of the inventive method.

FIG. 5 is a flowchart of a fourth embodiment of an inventive method for magnetic resonance imaging in an examination region of an examination object 15 by means of a magnetic resonance apparatus 11.

The following description is essentially limited to the differences from the exemplary embodiment in FIG. 3, with reference being made in respect of unchanging method steps to the description of the exemplary embodiment in FIG. 3. Method steps that essentially stay the same are basically numbered with the same reference numerals.

In contrast to the approach shown in FIG. 3, the at least one first shim channel 36 is not adjusted for the section before acquisition of the magnetic resonance image data from a section in a further method step 42 using the first shim parameter set ascertained in further method step 40. This embodiment also takes into account the influence of the at least one second shim channel 37 in the calculation of the first shim parameter sets for the at least one first shim channel 36. In contrast to the third embodiment according to FIG. 4, the field characteristic following adjustment of the at least one second shim channel 37 is not calculated, however, but actually scanned.

Instead, according to FIG. 5, a fourth B0 field map is acquired in a further substep 42-X of the further method step 42 following adjustment of the at least one second shim channel 37 in a first substep 42-1 of the further method step 42. The fourth B0 field map is acquired, in particular, at the earliest when the second settling time in a further substep 42-2 of further method step 42 has elapsed.

In a further substep 42-Y of further method step 42 a plurality of altered first shim parameter sets is then ascertained for the at least one first shim channel 36 using the fourth B0 field map. In a first sub-substep 42Y-1 of substep 42-Y an adjusted first shim parameter set is therefore ascertained for the first section, and in a second sub-substep 42Y-2 of substep 42-Y an adjusted second shim parameter set is ascertained for the second section. The result is again a center frequency $\Delta f_0''^{(1)}$, and a set of first shim parameter sets $\Delta G_x''^{(1)}$, $\Delta G_y''^{(1)}$, $\Delta G_z''^{(1)}$ for the at least one first shim channel 36 for each section.

The at least one first shim channel 36 is adjusted using the plurality of adjusted first shim parameter sets during acquisition of the magnetic resonance image data in further method step 42. In a third substep 42-3 of further method step 42 the at least one first shim channel 36 is therefore adjusted for the first section using the adjusted first shim parameter set. In a fifth substep 42-5 of further method step 42 the at least one first shim channel 37 is then adjusted for the second section using the adjusted second shim parameter set.

The first B0 field map and/or fourth B0 field map can be acquired using raw data which comprises at least three echo signals which are each acquired following an excitation of the examination region.

The method steps of the inventive method shown in FIG. 2-5 are performed by the computer 24. For this purpose, the computer 24 has the requisite software and/or computer programs that are stored in a memory of the computer 24. The software and/or computer programs comprise program means which are configured to carry out the inventive method when the computer program and/or the software are run in the computer 24 by operation of a processor of the computer 24.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for acquiring magnetic resonance (MR) data from an examination region of an examination object situated in an MR scanner that comprises a shim unit, said shim unit comprising a first shim channel volume having at least one first shim channel and a second shim channel volume having at least one second shim channel, said method comprising:

in a computer, dividing said examination region into multiple sections;

in said computer, determining a plurality of first shim parameter sets for said first shim channel, with one first shim channel parameter set among said plurality of first shim channel parameter sets being determined for each section among said multiple sections;

in said computer, determining a second shim parameter set for said second shim channel dependent on said plurality of determined first shim parameter sets;

before acquiring said magnetic resonance data from the examination region, adjusting said second shim channel using said second shim parameter set and adjusting said first shim channel for acquiring the magnetic resonance data from a specific section among said multiple sections using a first shim parameter set determined for that specific section; and operating said MR scanner to acquire MR data from said specific section using the adjusted first shim channel and the adjusted second shim channel.

2. A method as claimed in claim 1 wherein said first shim channel volume and said second shim channel volume are disjunct.

3. A method as claimed in claim 1 comprising, before determining said plurality of first shim parameter sets, operating said MR scanner to acquire a first B0 field map that represents a basic magnetic field in said MR scanner, and determining said plurality of first shim parameter sets using said first B0 field map.

4. A method as claimed in claim 3 comprising acquiring said first B0 field map using raw data comprising at least three echo signals that are respectively acquired following an excitation of nuclear spins in the examination region.

5. A method as claimed in claim 3 comprising, in said computer, calculating a second B0 field map using said first B0 field map and said plurality of first shim parameter sets, and determining said second shim parameter set using said plurality of first shim parameter sets and said second B0 field map.

6. A method as claimed in claim 5 comprising calculating said second B0 field map using said first B0 field map and said plurality of first shim parameter sets by offsetting B0 field contributions, resulting from said plurality of first shim parameter sets, against said first B0 field map.

7. A method as claimed in claim 6 comprising, in said computer, offsetting a spatial portion of said first B0 field map against said B0 field contributions against a determined first shim parameter set among said plurality of first shim parameter sets that has been specifically determined for said section among said multiple sections, that corresponds to said spatial portion.

8. A method as claimed in claim 5 comprising, in said computer, calculating a third B0 field map using said first B0 field map and said second shim parameter set, and determining a plurality of adjusted first shim parameter sets for said first shim channel using said third B0 field map, with said first shim channel being adjusted using said plurality of adjusted first shim parameter sets for acquiring said MR data.

9. A method as claimed in claim 1 comprising operating said MR scanner to acquire said MR data by sequential steps comprising:
adjusting said second shim channel using said second shim parameter set;
thereafter adjusting said first shim channel using a first shim parameter set determined for a first section among said multiple sections;
thereafter acquiring MR data from said first section;
thereafter adjusting said first shim channel using a first shim parameter set determined for a second section among said multiple sections; and
thereafter acquiring MR data from said second section.

10. A method as claimed in claim 9 comprising operating said MR scanner to cause a second settling time to elapse between adjustment of said second shim channel and acquiring said MR data from said first section, and to cause a first settling time to elapse between adjusting said first shim channel using said first shim parameter set and acquiring the MR data from the first section, with said first settling time being shorter than said second settling time.

11. A method as claimed in claim 9 comprising, after adjusting said second shim channel, operating said MR scanner to acquire a fourth B0 field map, and determining a plurality of altered first shim parameter sets for said first shim channel using said fourth B0 field map and, during acquisition of said MR data, adjusting said first shim channel using said plurality of altered first shim parameter sets.

12. A magnetic resonance (MR) apparatus comprising:
an MR scanner comprising a shim unit, said shim unit comprising a first shim channel volume having at least one first shim channel and a second shim channel volume having at least one second shim channel;
a computer configured to divide an examination region of an examination subject into multiple sections;
said computer being configured to determine a plurality of first shim parameter sets for said first shim channel, with one first shim channel parameter set among said plurality of first shim channel parameter sets being determined for each section among said multiple sections;
said computer being configured to determine a second shim parameter set for said second shim channel dependent on said plurality of determined first shim parameter sets;
said computer being configured to adjust, before acquiring said magnetic resonance data from the examination region, said second shim channel using said second shim parameter set and to adjust said first shim channel for acquiring the magnetic resonance data from a specific section among said multiple sections using a first shim parameter set determined for that specific section; and
said computer being configured to operate said MR scanner to acquire MR data from said specific section using the adjusted first shim channel and the adjusted second shim channel.

13. A non-transitory, computer-readable data storage medium encoded with programming instructions for operating a magnetic resonance (MR) apparatus to acquire MR data from an examination region of an examination object situated in an MR scanner of the MR apparatus that comprises a shim unit, said shim unit comprising a first shim channel volume having at least one first shim channel and a second shim channel volume having at least one second shim channel, said MR apparatus comprising a control computer and said programming instructions causing said control computer to:
divide said examination region into multiple sections;
determine a plurality of first shim parameter sets for said first shim channel, with one first shim channel parameter set among said plurality of first shim channel parameter sets being determined for each section among said multiple sections;
determine a second shim parameter set for said second shim channel dependent on said plurality of determined first shim parameter sets;
before acquiring said magnetic resonance data from the examination region, adjust said second shim channel using said second shim parameter set and adjust said first shim channel for acquiring the magnetic resonance data from a specific section among said multiple sections using a first shim parameter set determined for that specific section; and
operate said MR scanner to acquire MR data from said specific section using the adjusted first shim channel and the adjusted second shim channel.

* * * * *